April 19, 1966 J. H. CARSON Plant Pat. 2,622
DOGWOOD TREE
Filed Dec. 23, 1964
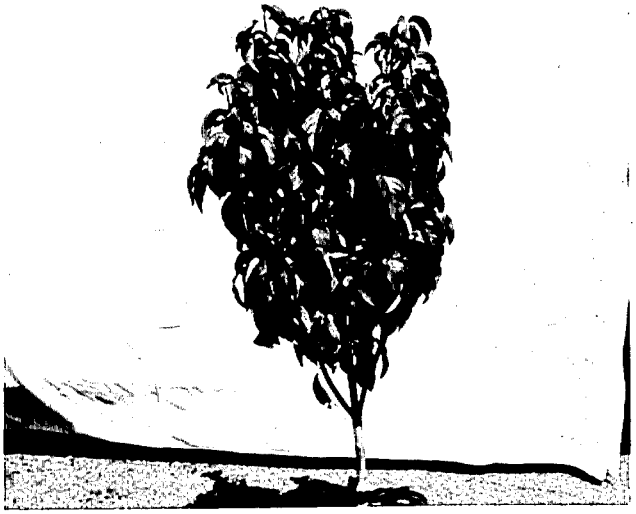
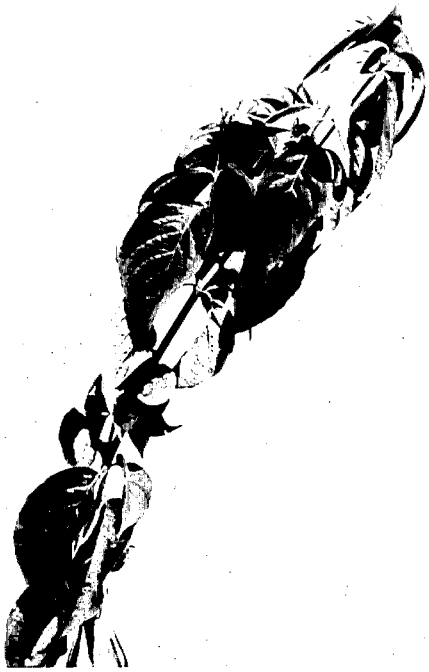
INVENTOR
James H. Carson
By: Lamont Johnston
ATTORNEY.

United States Patent Office

Plant Pat. 2,622
Patented Apr. 19, 1966

2,622
DOGWOOD TREE

James H. Carson, Winchester, Tenn., assignor to
Gale M. Carson, Winchester, Tenn.

Filed Dec. 23, 1964, Ser. No. 420,847
1 Claim. (Cl. Plt.—51)

My invention relates to a new and distinct cultivar of *Cornus florida*, or flowering dogwood tree, originating as an open pollinated, or chance, seedling from plants of *Cornus fluorida* in my nursery in Winchester, Tennessee.

My new cultivar was selected for its distinct, dark green, glossy foliage, compact habit of growth, and its drought resistance.

Asexual propagation by budding of this new plant as performed in my nursery at Winchester, Tennessee, shows that this plant reproduced true to form with the above characteristics transmitted through succeeding propagations.

The accompanying illustrations show in natural color typical foliage and the entire plant of this new cultivar.

References to color in the following description indicate the Horticultural Colour Chart, issued by the British Colour Council and the Royal Horticultural Society. Where there are other references to color, the ordinary dictionary meanings of the terms are intended.

*The plant*

Growth habit: A vigorous compact plant under good cultural conditions. Form is typical of common flowering dogwood, being a small tree, but with more upright branches and more drought resistance than common dogwood.

Foliage: Leaves—opposite, simple, deciduous, ovate, 4 to 5½" long, 2 to 3" wide, margin entire, petioles ¼ to ⅜" long.

Color: Mature leaves Scheeles Green 860, glossy, leathery or thick texture. Lower surface of mature leaves light green with heavy bloom appearing as Lavender Green 00761/2 on the lower surface. Foliage stays dark green later than other cultivars. Fall foliage color is purplish red.

Flowers: Blooming at same time as common flowering dogwood. Bracts are somewhat larger than typical, being 3½" to 4½" across. Bracts are white, with a rusty red margin at the apical end and small blotches of rusty red color throughout the entire bract. Flowers are freely produced on young plants.

Fruits: Typical fruit clusters. Individual drupes are Cardinal Red 822 in color.

Branches: One year old branches are similar to typical flowering dogwood in green color, but are more upright and compact, with shorter internodes.

Disease and pest resistance: Good resistance to disease and insects as observed under field conditions and compared with other cultivated dogwoods.

Hardiness: Hardy without protection in Zone 6, as shown in the Plant Hardiness Zone Map, Miscellaneous Publication No. 824, Agricultural Research Service, U.S.D.A. Additional hardiness zones to be determined in the future. As to hardiness, there was no winter damage at temperatures to −15° F. to plants in this cultivar in our nursery.

*Comparison*

This new cultivar differs from common white flowering dogwood as follows:

(1) Mature leaves glossy Scheeles Green 860 in color.

(2) Compact habit of growth with upright branches and short internodes.

(3) Plants more drought resistant than other cultivars and maintaining good dark green foliage throughout the summer and early fall.

I claim:

A new and distinct variety of flowering dogwood tree substantially as herein shown and described, characterized particularly by the compact growth habit, drought resistance, and dark green foliage.

No references cited.

ABRAHAM G. STONE, *Primary Examiner.*

R. E. BAGWILL, *Assistant Examiner.*